(12) United States Patent
Castro

(10) Patent No.: US 6,599,236 B1
(45) Date of Patent: Jul. 29, 2003

(54) DILDO

(76) Inventor: Floyd F. Castro, 5377 Sunrise Meadows La., Oakey, CA (US) 94561

( * ) Notice: Subject to any disclaimer, the term of this patent is extended or adjusted under 35 U.S.C. 154(b) by 0 days.

(21) Appl. No.: 09/712,663

(22) Filed: Nov. 15, 2000

(51) Int. Cl.$^7$ .................................................. A61F 5/00
(52) U.S. Cl. ............................................................ 600/38
(58) Field of Search ....................... 600/38–41; 601/15, 601/18

(56) References Cited

U.S. PATENT DOCUMENTS

| | | | | |
|---|---|---|---|---|
| 547,076 A | * | 10/1895 | Hubbell | 601/15 |
| 1,551,499 A | * | 8/1925 | Homan | 126/263.03 |
| 1,628,272 A | * | 5/1927 | Reitz | 601/18 |
| 1,690,926 A | * | 11/1928 | Dequer | 601/18 |
| 1,729,044 A | * | 9/1929 | Kirk et al. | 126/263.05 |
| 2,387,258 A | * | 10/1945 | Hague | 165/46 |
| 2,863,445 A | * | 12/1958 | Johnson | 601/18 |
| 4,502,469 A | * | 3/1985 | Jaw | 601/15 |
| 5,439,007 A | | 8/1995 | Fischer | |
| 5,676,637 A | * | 10/1997 | Lee | 601/134 |
| 5,725,473 A | | 3/1998 | Taylor | |
| 6,056,705 A | | 5/2000 | Stigar-Brown | |
| 6,358,273 B1 | * | 3/2002 | Strul et al. | 607/101 |

* cited by examiner

Primary Examiner—Samuel G. Gilbert

(57) ABSTRACT

A dildo having a shaft and an arrangement for heating the shaft to a temperature which provides improved sexual stimulation to a user. In one embodiment the heating is provided by a charge of heated liquid contained in a cavity within the shaft. The liquid is heated externally and then put into the cavity, or in another embodiment it can be heated within the cavity by a coil of electrical resistance heating wire. In another embodiment a wire coil embedded in the shaft material is heated by electric power.

2 Claims, 1 Drawing Sheet

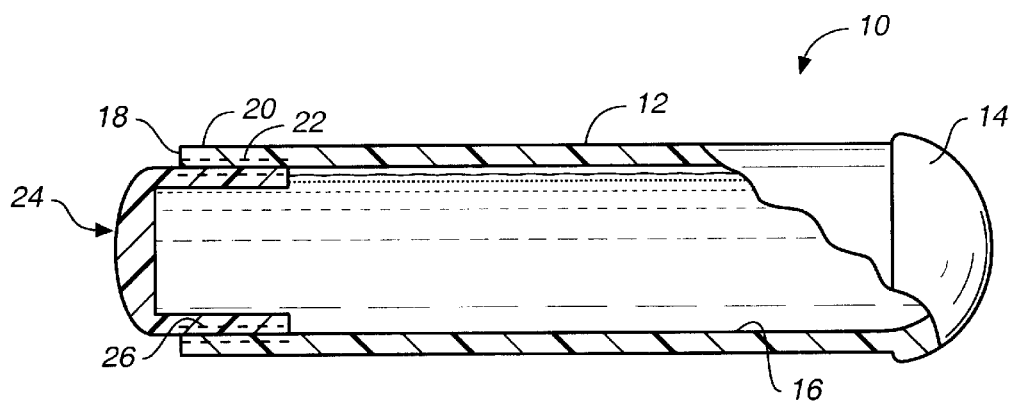
FIG._1
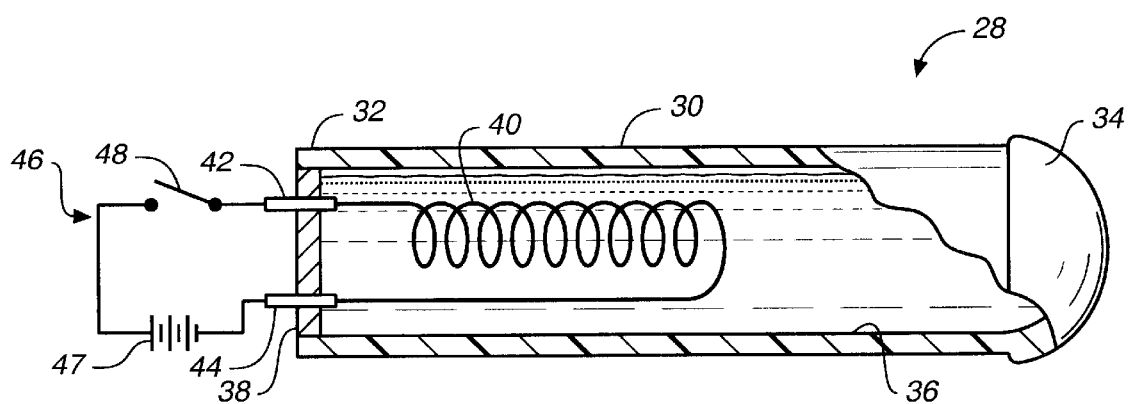
FIG._2
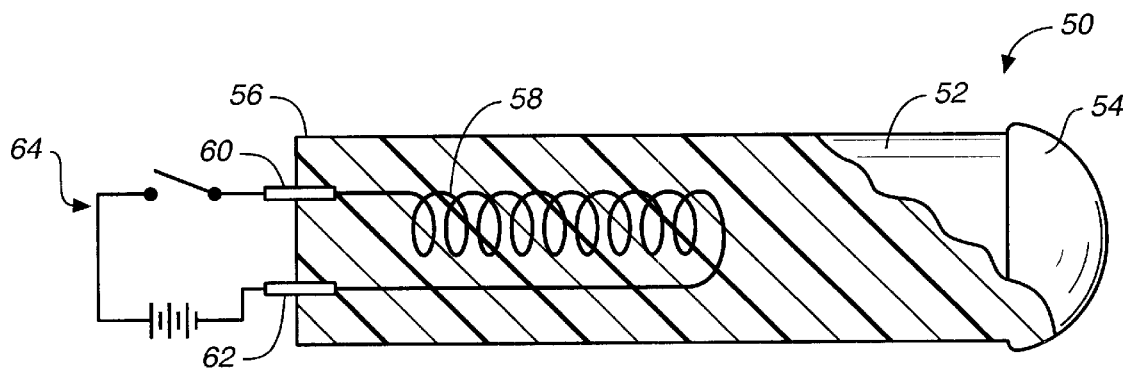
FIG._3

DILDO

BACKGROUND OF THE INVENTION

1. Field of the Invention

This invention relates in general to sexual aid devices, and more particularly to dildos.

2. Description of the Related Art

Dildos have been commonly used for sexual aid by stimulation of erogenous zones of the human body. Examples included the use of dildos for clitoral stimulation or for insertion into body orifices, such as the vagina.

Convention dildos have included means for increasing the degree of stimulation, such as means for inducing vibration or vacuum on the user's body and which operate in conjunction with manipulation of the dildo. Among the disadvantages and shortcomings of conventional dildos are that they do not provide self-contained means for warming the dildo, and particularly warming to a temperature at or near that of the human body. Relatively cold dildos are uncomfortable in use so as to detract from the user's sexual stimulation. Dildos which can be warmed in a self-contained manner are desirable in that they would be more easy to use, they would increase the degree of sexual stimulation and would add to the user's pleasure.

The need has therefore been recognized for a dildo which obviates the foregoing and other limitations and disadvantages of prior art dildos. Despite the various dildo apparatus in the prior art, there has heretofore not been provided a suitable and attractive solution to these problems.

SUMMARY OF THE INVENTION

The invention provides a dildo having a self-contained arrangement which warms the dildo to a temperature which is sufficient to provide more sexual stimulation and make its use more pleasurable.

The foregoing and other advantages, objects and features of the invention will appear from the following description of the several embodiments in conjunction with the accompanying drawings.

BRIEF DESCRIPTION OF THE DRAWINGS

FIG. 1 is side elevation view, partially broken away, of a dildo in accordance with one embodiment of the invention.

FIG. 2 is side elevation view, partially broken away, of a dildo in accordance with another embodiment.

FIG. 3 is side elevation view, partially broken away, of a dildo in accordance with another embodiment.

DESCRIPTION OF THE PREFERRED EMBODIMENTS

In the drawings, FIG. 1 illustrates generally at 10 a dildo in accordance with one preferred embodiment of the invention. Dildo 10 is comprised of a hollow shaft 12 which is cylindrical, preferably of circular cross-section. The dildo can be made of any desired material, and preferably the material is soft and compliant, such as rubber or a synthetic polymer. Also, the dildo could be of composite construction with a firm inner core and a relatively softer outer layer suitable for comfortable contact with the human body.

The shaft has a distal end 14 which can be shaped in conformance with the end of the glans penis of the human male.

The shaft has an internal cavity 16 which is accessible through an opening 18 at a proximal end 20 of the shaft. Internal threads 22 are formed within the proximal end on the inside of the shaft. The cavity is capable of containing a charge 23 of warm liquid, such as water which heats the shaft by conduction. While opening 18 is shown at the proximal end, the invention contemplates a construction in which access to the cavity for filling or removing the liquid is by an opening on a side of the shaft and in which the opening would be closed by a suitable plug.

An end cap 24 has external threads 26 which are sized and proportioned for threading into internal threads 22 to form a tight seal with the shaft and thereby releasably seal the liquid within the cavity. When it desired to initially heat, or to reheat, the dildo, end cap 24 can be easily unscrewed to enable the user to pour the cooler liquid out and refill the cavity with another charge of heated liquid. The charge of liquid is heated to a desired temperature which is sufficient to be comfortable to the user while providing increased sexual stimulation. For this purpose the liquid temperature can be at or near the normal temperature of the human body, which is about 98° F.

FIG. 2 illustrates generally at 28 a dildo in accordance with another preferred embodiment of the invention. Dildo 28 is comprised of a cylindrical shaft 30 having a proximal end 32 and a distal end 34, which can be shaped as described for the embodiment of FIG. 1. The shaft has an internal cavity 36 which is sealed at the proximal end by a wall 38. A charge of liquid, such as water, is contained within the cavity. For permanently sealing the charge, wall 38 is fixedly attached to the shaft by suitable means such as integral molding, adhesive, thermal welding or sonic bonding. As desired the wall could be detachable by means such as a threaded connection, as described for the embodiment of FIG. 1.

A coil 40 of electrical resistant heating wire is mounted within cavity 36 and immersed in the liquid. The ends of the coil are connected with respective terminals 42, 44 which project through wall 38. When the user desires to heat the liquid, and thereby indirectly heat the dildo shaft, the terminals are connected to a suitable source of electric power, shown schematically by the circuit 46 comprising a battery 47 and on-off switch 48. A suitable thermostat, not shown, could be employed in the circuit to limit heating of the coil to the desired temperature.

FIG. 3 illustrates another embodiment providing a dildo 50 having a shaft 52 with a distal end 54 and proximal end 56. This shaft is formed of a desired soft and compliant material that is uniform across the shaft without any cavity. A coil 58 of electrical resistant heating wire is embedded within the shaft material. The coil ends are connected with terminals 60 and 62 which in turn are connectable with an electric power source comprising the battery and switch circuit 64. With the circuit closed, the coil is heated to indirectly heat the dildo shaft.

While the foregoing embodiments are at present considered to be preferred, it is understood that numerous variations and modifications may be made therein by those skilled in the art and it is intended to cover in the appended claims all such variations and modifications as fall within the true spirit and scope of the invention.

What is claimed is:

1. A dildo for use in providing improved sexual stimulation to a human, the dildo comprising the combination of a cylindrical shaft having a proximal end and a distal end, the shaft has an internal cavity, and heating means in the shaft for heating the shaft to a temperature sufficiently near the temperature of the human body to provide sexual stimulation, the heating means comprises a liquid heated to said temperature, the cavity is adapted to contain the liquid, a coil of electric resistance heating wire is immersed in the liquid, and terminal means for connecting the coil to a source of electric power.

2. A dildo as in claim 1 in which the cavity is liquid sealed, and the terminal means extends through the proximal end of the shaft.

\* \* \* \* \*